United States Patent [19]

Mische

[11] Patent Number: 5,792,106
[45] Date of Patent: Aug. 11, 1998

[54] IN SITU STENT FORMING CATHETER

[75] Inventor: Hans A. Mische, St. Cloud, Minn.

[73] Assignee: Scimed Life Systems, Inc., Maple Grove, Minn.

[21] Appl. No.: 785,799

[22] Filed: Jan. 21, 1997

Related U.S. Application Data

[63] Continuation of Ser. No. 532,256, Sep. 22, 1995, abandoned, which is a continuation of Ser. No. 160,589, Dec. 2, 1993, abandoned.

[51] Int. Cl.$^6$ .................................................. A61M 29/00
[52] U.S. Cl. ............................ 604/96; 604/265; 606/194
[58] Field of Search ........................... 604/890.1, 891.1, 604/8, 96, 101, 265, 266, 21; 623/1, 12, 66, 13; 606/191, 192, 194, 198

[56] References Cited

U.S. PATENT DOCUMENTS

| | | |
|---|---|---|
| 4,553,545 | 11/1985 | Maass et al. |
| 4,624,847 | 11/1986 | Ayer et al. |
| 4,740,207 | 4/1988 | Kreamer |
| 4,820,298 | 4/1989 | Leveen et al. |
| 4,838,269 | 6/1989 | Robinson et al. |
| 4,856,516 | 8/1989 | Hillstead |
| 4,878,906 | 11/1989 | Lindemann et al. |
| 4,913,141 | 4/1990 | Hillstead |
| 4,943,278 | 7/1990 | Euteneuer et al. |
| 4,994,033 | 2/1991 | Shockey et al. |
| 5,032,113 | 7/1991 | Burns |
| 5,049,132 | 9/1991 | Shaffer et al. .................. 604/101 |
| 5,059,178 | 10/1991 | Ya ................................ 604/96 |
| 5,059,211 | 10/1991 | Stack et al. |
| 5,078,736 | 1/1992 | Behl |
| 5,087,244 | 2/1992 | Wolinsky et al. |
| 5,100,429 | 3/1992 | Sinofsky et al. ............... 604/96 |
| 5,112,305 | 5/1992 | Barath et al. .................. 604/96 |
| 5,213,576 | 5/1993 | Abiuso et al. ................. 604/96 |
| 5,213,577 | 5/1993 | Kratzer ........................ 606/194 |
| 5,213,580 | 5/1993 | Slepian et al. ................ 623/1 |
| 5,232,444 | 8/1993 | Just et al. |
| 5,254,089 | 10/1993 | Wang .......................... 604/96 |
| 5,256,141 | 10/1993 | Gencheff et al. ............... 604/101 |
| 5,261,875 | 11/1993 | Spears ......................... 604/101 |
| 5,279,546 | 1/1994 | Mische et al. ................. 604/101 |
| 5,286,254 | 2/1994 | Shapland et al. ............... 604/20 |
| 5,318,531 | 6/1994 | Leone ......................... 604/101 |
| 5,320,604 | 6/1994 | Walker et al. ................. 604/96 |
| 5,328,470 | 7/1994 | Nabel et al. .................. 604/101 |
| 5,328,471 | 7/1994 | Slepian ....................... 604/101 |
| 5,336,178 | 8/1994 | Kaplan et al. ................. 604/96 |
| 5,344,419 | 9/1994 | Spears |
| 5,344,444 | 9/1994 | Glastra |

FOREIGN PATENT DOCUMENTS

94/21320  9/1994  WIPO.

OTHER PUBLICATIONS

Dorland's Illustrated Medical Dictionary, 24th Edition 1965, p. 1438.

Improved Dilatation Catheter Balloons, by Stanley B. Levy, Ph.D., *Journal of Clinical Engineering*, vol. 11, No. 4, Jul.–Aug., 1986, pp. 291–296.

Intravascular Stenting for Stenosis of Aortocoronary Venous Bypass Grafts, Philip Urban, M.D., et al., *JACC*, vol. 13, No. 5, Apr. 1989, pp. 1085–1091.

Results of Intracoronary Stents for Management of Coronary Dissection After Balloon Angioplasty, Michael Haude, M.D., et al., *The American Journal of Cardiology*, vol. 67, Apr. 1, 1991, pp. 691–696.

Vascular Stents, Schatz, *Circulation*, vol. 79, No. 2, Feb. 1989, pp. 449–457.

Circle 248 For Reader Service, paragraph on cyanoacrylates.

Synthetic polymer tissue adhesive in the surgery of ascending aortic dissection, Steven Griffin, M.D., et al., *J. Cardiovasc. Surg.*, 31, 1990, pp. 239–241.

Nexaband® Clinical Applications Up Date No. 4S, Advertisement for Nexaband Liquid n–butyl cyanoacrylate.

Nexaband® Avian: Clinical Applications Update No. 5S, Advertisement for Hexaband Avian n–butyl cyanoacylate, Tri–Point Medical L.P., Jun. 1990.

*Primary Examiner*—Ronald K. Stright, Jr.
*Attorney, Agent, or Firm*—Vidas, Arrett & Steinkraus

[57] ABSTRACT

A curable fluid material is caused to flow out of the balloon in a balloon catheter, through perforations therein, to form a stent in situ in the PTCA procedure.

17 Claims, 6 Drawing Sheets

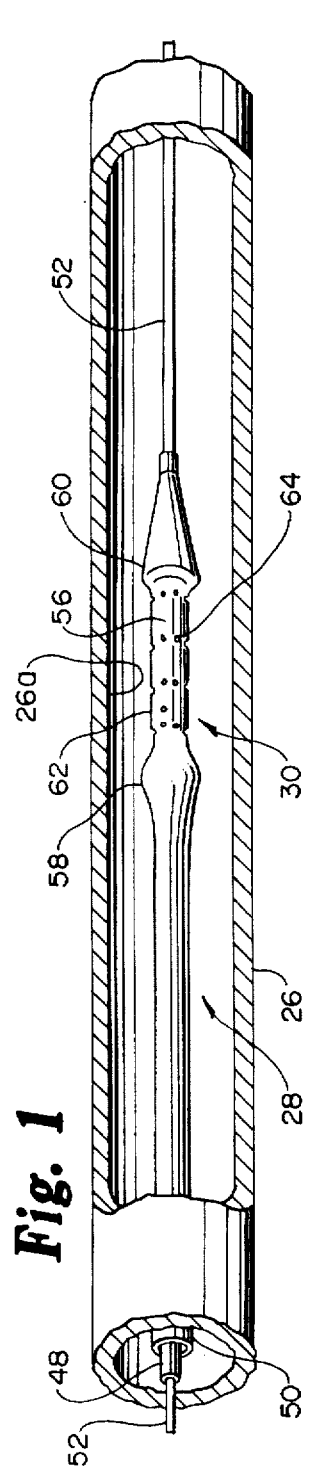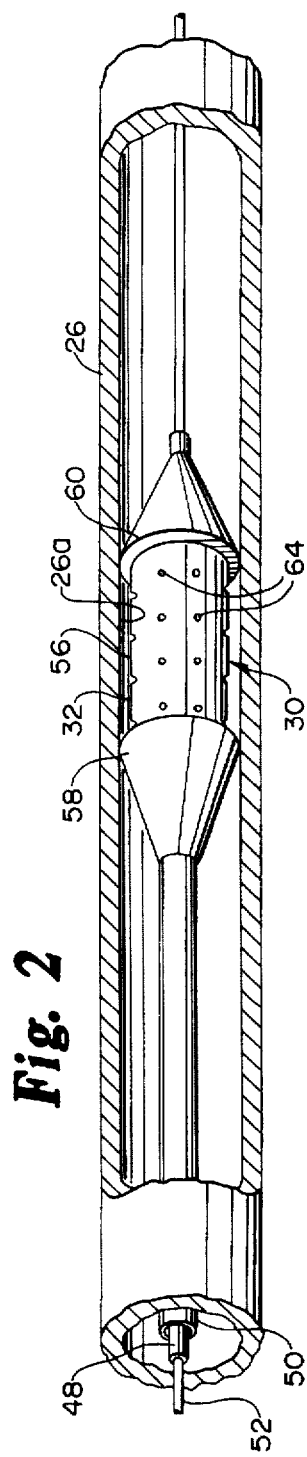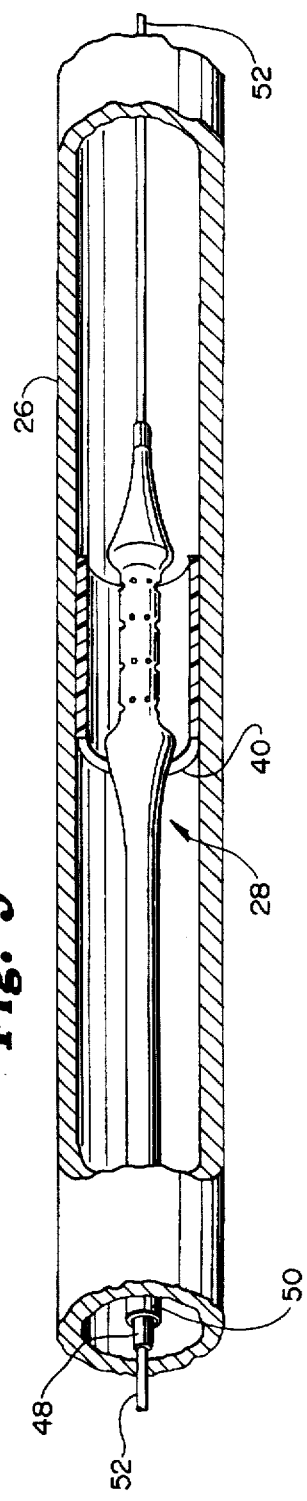

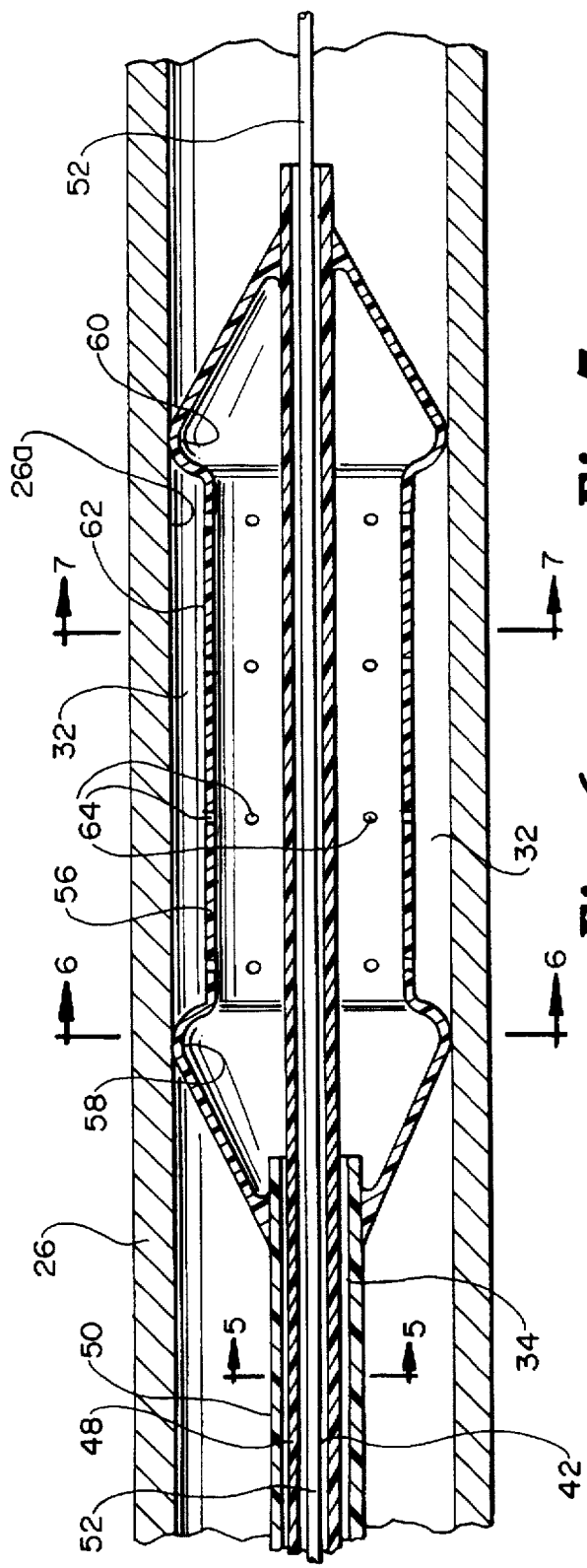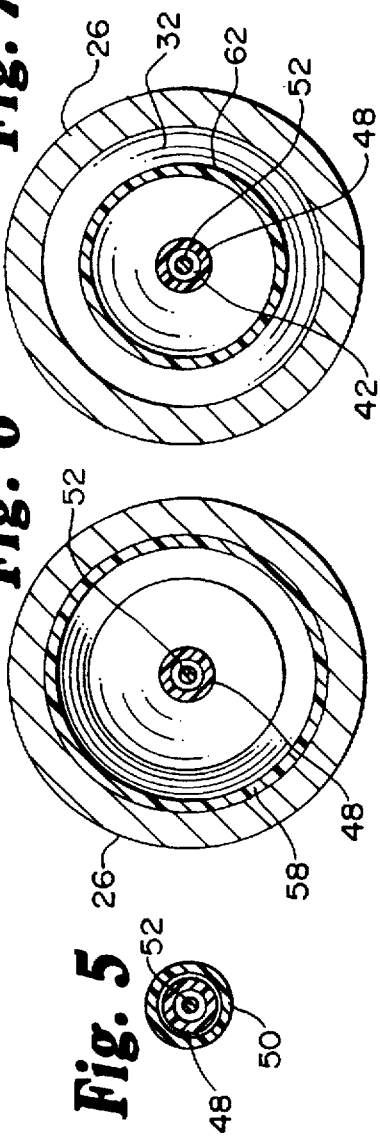

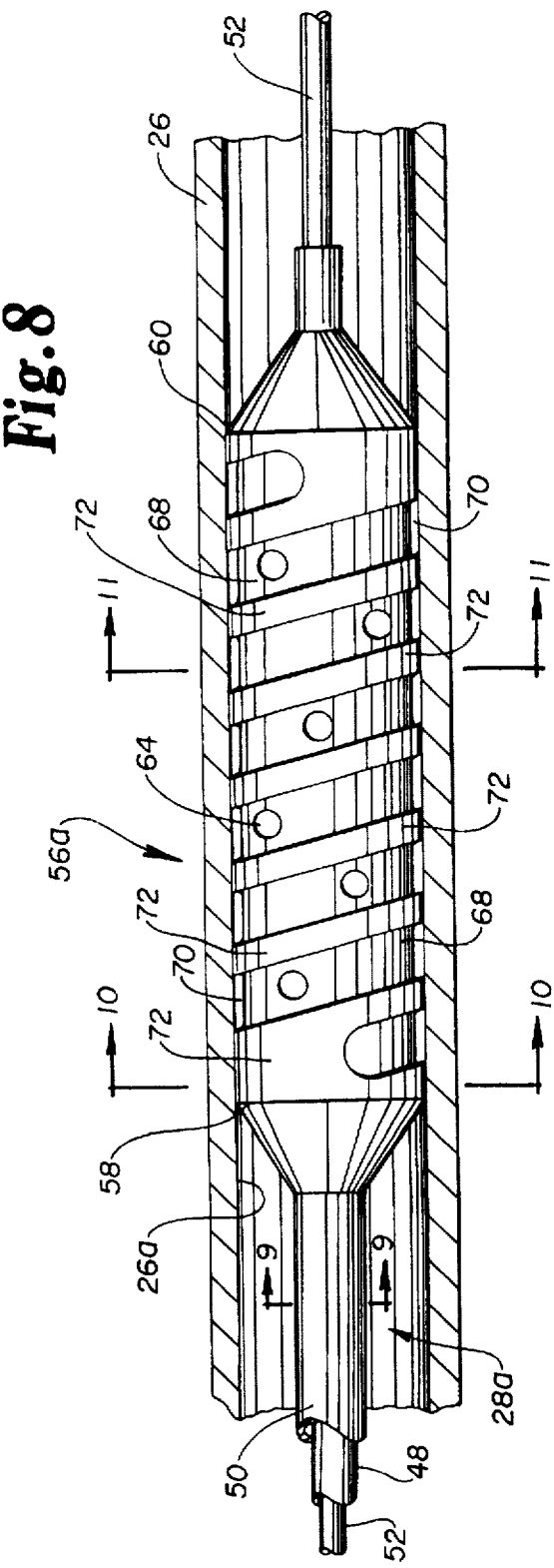
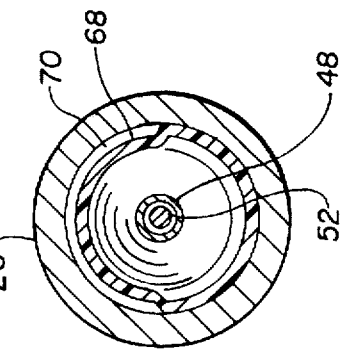
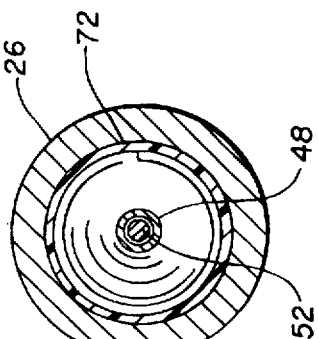
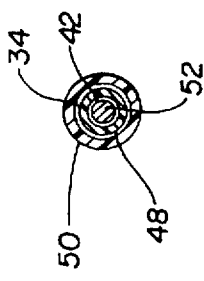

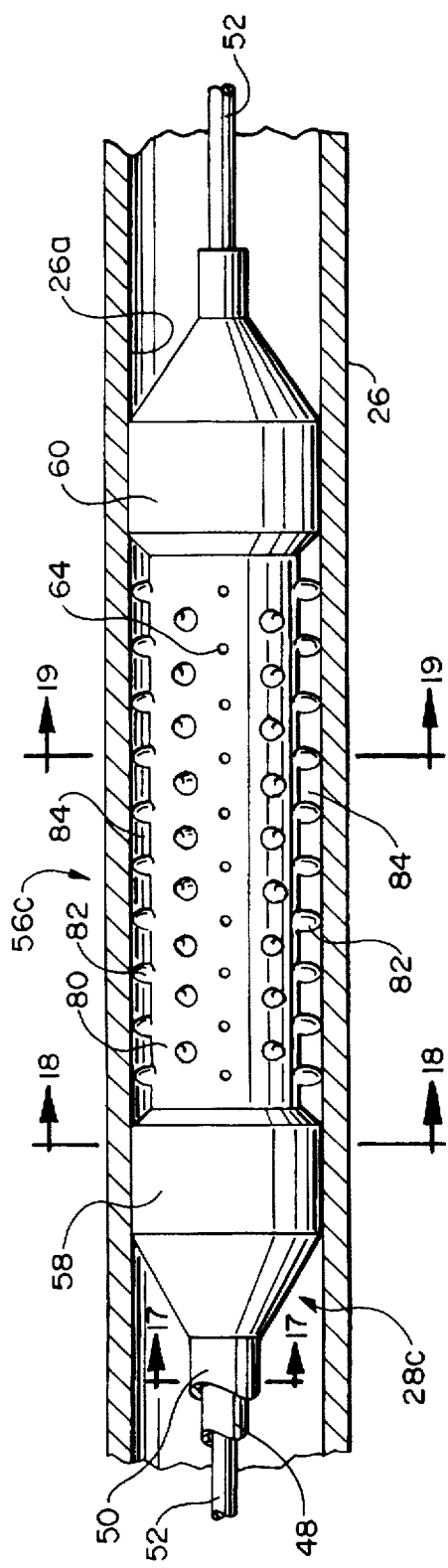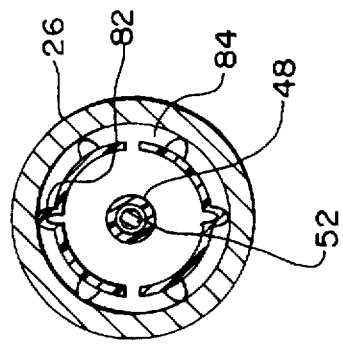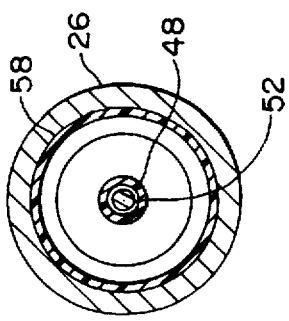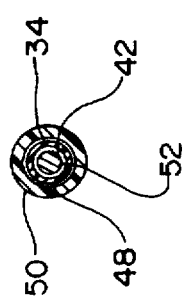

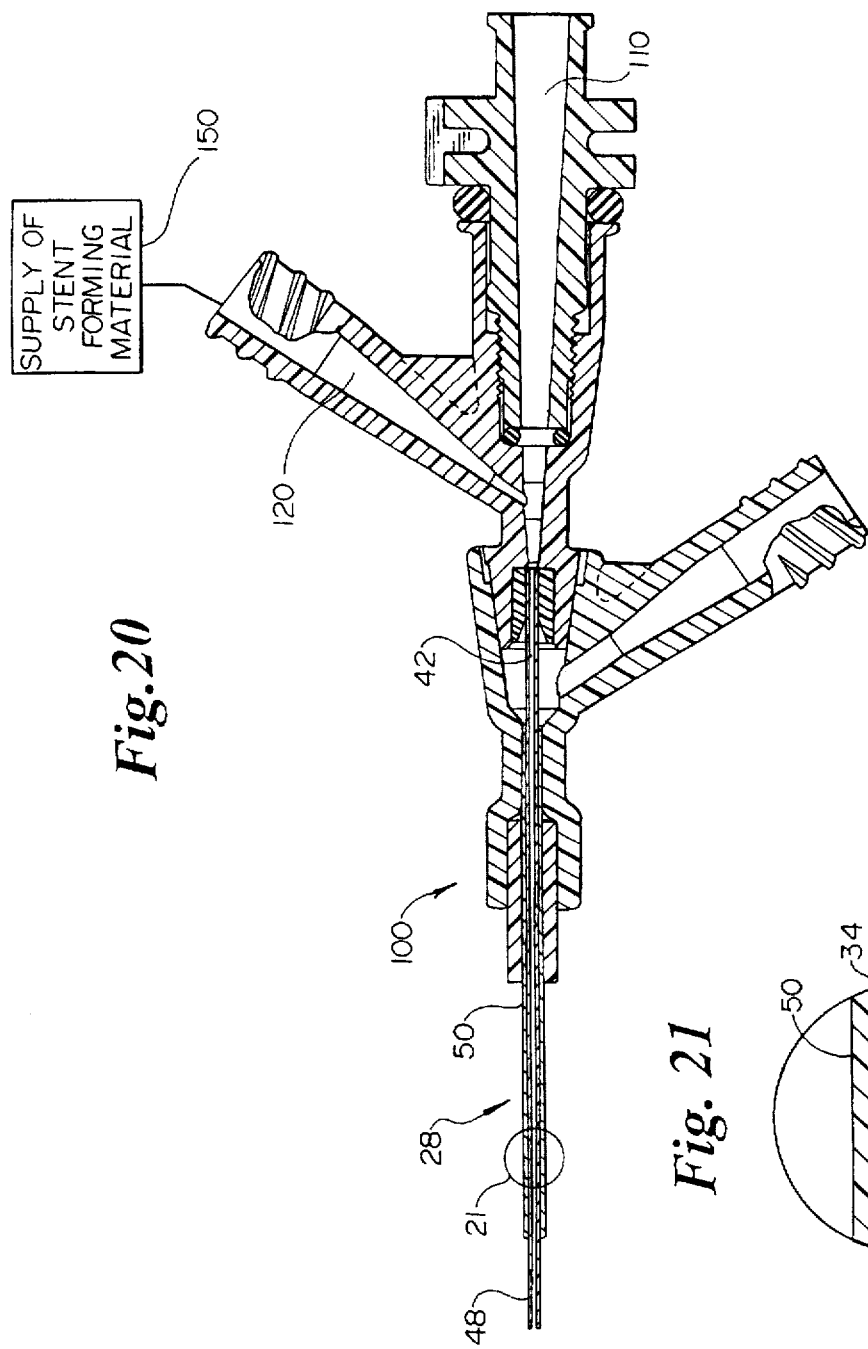

IN SITU STENT FORMING CATHETER

This is a continuation of copending application Ser. No. 08/532,256 filed on Sep. 22, 1995, now abandoned which is a continuation of Ser. No. 08/160,589 filed on Dec. 2, 1993, now abandoned.

BACKGROUND OF THE INVENTION

The present invention relates in general to a device and method for delivering fluid materials to the human vascular system. More particularly, it relates to a novel catheter device and method for delivering drugs and other fluid material to an isolated area of a human vessel.

Obstructive atherosclerotic diseases typically result from the build up of fatty substances, known generally as lesions or stenoses, on the interior walls of the human vascular system. These deposits reduce the inside diameter of vessels and thereby restrict blood flow.

One commonly used method for treating coronary atherosclerosis is a procedure known as coronary artery bypass graft surgery ("bypass surgery"). Bypass surgery, however, is extremely invasive and poses a high level of risk to the patient. Thus, less invasive and traumatic procedures, such as angioplasty or atherectomy, are usually considered before resorting to bypass surgery.

In a typical percutaneous transluminal coronary angioplasty (PTCA) procedure, a guiding catheter is introduced at an appropriate location in the human body and routed through the vascular system into the aorta and coronary orifice. In one form of this procedure a relatively flexible guidewire is advanced through the guiding catheter to the artery, and then steered into side branches (if necessary) to access the lesion. Once the guiding catheter and guidewire have established a path across the lesion, an "over-the-wire" dilatation balloon catheter is passed over the guidewire by inserting the proximal end of the guidewire into the distal end of the balloon catheter and then pushing the balloon catheter over the guidewire until the balloon is adjacent the lesion. In another form, the balloon catheter and guide wire are integral and are "loaded" together. The balloon is then inflated by introducing a fluid into the balloon through an inflation lumen in the catheter's shaft. The inflated balloon expands against the blockage to dilate the obstructed blood vessel. In yet another type of balloon catheter known as "fixed-wire," the need for a separate guidewire is eliminated by attaching a short flexible guidewire to the distal end of the catheter.

Further details of angioplasty procedures and the devices used in such procedures are found in U.S. Pat. No. 4,983,278 (Euteneuer), and U.S. Pat. No. 5,032,113 (Burns). The entire disclosure of each of these patents is incorporated herein by reference.

In atherectomy, a miniaturized cutting tool is attached to the end of a small diameter flexible catheter and maneuvered through the patient's vascular system to the lesion. The cutting tool is used to cut and remove the lesion from the vessel wall.

Angioplasty and atherectomy procedures, however, do not always achieve lasting results. Following either of these procedures, the diseased blood vessel may recoil or restenosis may occur. Other post-procedure concerns include vasoconstriction, vasospasm, or the possibility of an intimal flap occurring. Also, it may be necessary in some instances to abort or "bail-out" of an angioplasty or atherectomy procedure. In these situations, a device known as a stent may be placed inside the vessel to provide additional support at the desired region. Stents are typically hollow cylindrical devices which have sufficient size and rigidity to maintain the diameter of the vessel, while at the same time allowing body fluid to pass.

In some situations, it is desirable to permanently implant a stent in the patient's vascular system. Examples of permanent stents are shown in U.S. Pat. Nos. 4,913,141; 4,878,906; 4,856,516; and 4,820,298. However, known permanent stents often require a relatively complicated installation procedure and may result in extended hospital stay and recovery time. Over time, the lesion, thrombus, etc. may grow back through and over the stent. Drug therapy may also be needed to offset any unfavorable reactions to the long term presence of the stent, particularly if the stent is made of metal.

Restenosis may also be combatted by administering a drug to the patient. The drug may be administered "systemically," which means that the drug is introduced, either orally or intravenously, into the vascular system and circulated throughout the body. Some drugs that have been tested in human clinicals include: heparin, calcium channel blockers, angiotensin converting enzyme inhibitors, fish oil, and growth peptides. Other agents have not been tried in clinicals, but are of interest. These include: thromboxane synthetase inhibitor, serotonin antagonists, HMGCoA reductase inhibitors, platelet derived growth factors, inflammatory cell factors, platelet aggregation inhibitors, and thrombin inhibitors such as hirudin or its analogs.

One of the problems with systemic administration is the inability to deliver a high enough concentration of the drug to the lesion. In the in vitro studies which have shown some success, a high concentration of the agent was used. Thus, it is believed that if the agent was delivered directly to the site, as opposed to systemically, it may be delivered at a high enough concentration to truly effect the physiologic response.

The reason many of these agents have not been used in higher concentrations in vivo in humans is that many of the agents tend to induce undesirable side effects in the patient. Thus, if high concentrations of the agents are given systemically, they may have unwanted physiologic effects. Therefore, if the drug can be given in high concentrations locally to the vessel wall while minimizing the vascular circulation of drug, the desired result of modulating the restenotic growth while preventing any unwanted systemic effects may be achieved.

One method of delivering drugs to a specific site is the use of a perforated or weeping balloon. An example of such is disclosed in U.S. Pat. No. 5,087,244 (Wolinsky, et al.). Also, U.S. patent application Ser. No. 07/740,047, filed Aug. 2, 1991, now abandoned and assigned to the assignee of this application, discloses a drug delivery catheter.

Perfusion is very important in developing a suitable fluid delivery means. It is necessary that the device be capable of safely delivering the agent over an extended period of time, and therefore, devices which occlude blood flow during delivery may not provide the necessary safety. Current research indicates that the initial restenosis events begin immediately after injury and continue intensely for several hours. Thus, it is desirable for the drug delivery system to be capable of safely delivering drugs for several hours, months, or possibly years, beginning immediately after intervention. This research also points out that the initial restenosis events may create a cascade of subsequent events that ultimately lead to intimal thickening. While these accumulations or lesions do not become apparent for several months, it is felt that if the initial restenosis events can be modulated or blocked, then the subsequent cascade can be altered, and a diminished overall thickening can be achieved.

Therefore, it is an object of the present invention to provide a device and method for forming a stent in situ.

It is another object of the present invention to provide a device which can form a stent in situ wherein the stent allows the free flow of blood through the vessel in which it is employed.

It is a further object of this invention to provide a device which forms a biodegradable stent in situ.

It is a still further object of this invention to provide a device which can form a stent in situ, wherein the stent delivers an agent to the delivery site over time.

SUMMARY OF THE INVENTION

To achieve these and other objects, the present invention provides a new and unique in situ stent forming device which may be inserted into a vessel, such as a blood vessel, for forming a stent inside a vessel wall. The stent is delivered to the desired site in fluid form and allowed to harden. The device includes an elongated tubular member having a proximal end, a distal end and a lumen. An inflatable balloon member is attached at the distal end of the tubular member and placed in fluid communication with the lumen. The outer surface of the balloon member is contoured such that it defines at least two spaced ridge seals. When the balloon is inflated, the spaced ridge seals, and the vessel wall define an isolation zone. At least one infusion port is provided on the balloon surface and in fluid communication with the lumen via the interior of the balloon. At least one fluid injection port is in fluid communication with the lumen at the proximal end of the tubular member.

The present invention also encompasses a method of using the in situ stent forming device to deliver drugs to a treatment site in desired concentrations.

The present invention provides a prolonged time frame for drug delivery in relatively high concentrations.

Further, the device and method of the present invention may be advantageously used to repair problems sometimes associated with angioplasty.

BRIEF DESCRIPTION OF THE DRAWINGS

FIG. 1 illustrates an in situ stent forming catheter embodying the present invention. The catheter is shown deflated inside a body vessel;

FIG. 2 further illustrates the catheter shown in FIG. 1 wherein the balloon portion of the catheter is inflated;

FIG. 3 further illustrates the catheter shown in FIG. 1 after it has formed a stent inside the vessel;

FIG. 4 is a longitudinal cross sectional view of the inflated catheter shown in FIGS. 2;

FIG. 5 is a cross sectional view of the inflated catheter shown in FIG. 4, taken along line 5—5;

FIG. 6 is a cross sectional view of the inflated catheter shown in FIG. 4, taken along line 6—6;

FIG. 7 is a cross sectional view of the inflated catheter shown in FIG. 4, taken along line 7—7;

FIG. 8 illustrates another in situ stent forming catheter embodying the present invention. The catheter is shown inflated inside a body vessel;

FIG. 9 is a cross sectional view of the catheter shown in FIG. 8, taken along line 9—9;

FIG. 10 is a cross sectional view of the catheter shown in FIG. 8, taken along line 10—10;

FIG. 11 is a cross sectional view of the catheter shown in FIG. 8, taken along line 11—11;

FIG. 16 illustrates another in situ stent forming catheter embodying the present invention. The catheter is shown inflated inside a body vessel;

FIG. 17 is a cross sectional view of the catheter shown in FIG. 16, taken along line 17—17;

FIG. 18 is a cross sectional view of the catheter shown in FIG. 16, taken along line 18—18.

FIG. 19 is a cross sectional view of the catheter shown in FIG. 16, taken along line 19—19.

FIG. 20 is a horizontal sectional view of a manifold which may be used with the device of the present invention, and FIG. 21 is an enlarged fragmentary view of the device of the present invention along circle 21 of FIG. 20.

DETAILED DESCRIPTION OF THE PREFERRED EMBODIMENT

Figure 12:
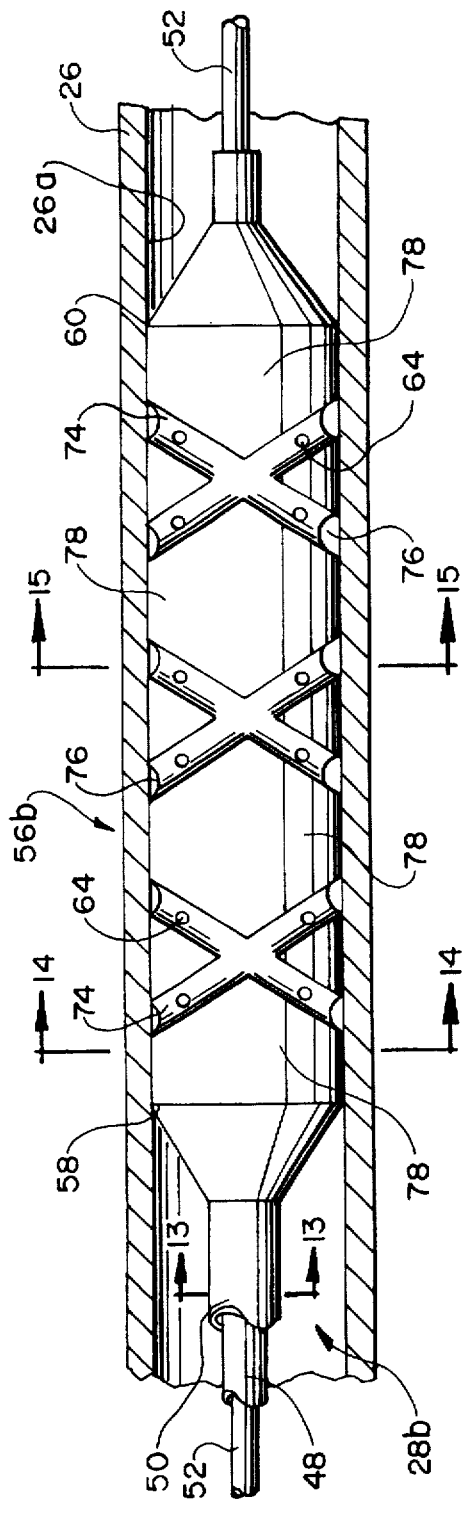
FIG. 12 illustrates another in situ stent forming catheter embodying the present invention. The catheter is shown inflated inside a body vessel.

Referring now to the drawings, and particularly to FIGS. 1–7, a catheter generally indicated at 28 embodying the features of the present invention is shown inside a body vessel 26, such as a blood vessel. Catheter 28 includes an inflatable balloon assembly generally indicated at 30 and located at the distal end of the catheter. As best seen in FIG. 2, when the balloon assembly 30 is inflated inside a human vessel 26, it defines a substantially cylindrical chamber 32 between balloon assembly 30 and the interior vessel wall 26a. Catheter 28 delivers a fluid substance to the cylindrical chamber 32 via an internal passageway or lumen 34 (seen in FIG. 4) which extends through the length of catheter 28 and terminates at a series of openings 64 in balloon assembly 30. The fluid may be pumped through catheter 28 by a conventional balloon catheter inflation arrangement (not shown). In one aspect of the invention, the fluid substance is of a type which hardens under certain body conditions existing external to the catheter. For example, a moisture curing polymeric material such as a cyanoacrylate may be used, the moisture being supplied by the body. Such a preferred cyanoacrylate is N-butyl-2-cyanoacrylate. Also, materials such as polymethyl acrylate (PMA) and polyaglycolic acid (GA), which are moisture curable when in an appropriate solvent based system (which are well known) may be used. Thus, once the fluid leaves the catheter and is delivered to fill chamber 32, it hardens, thereby forming a hollow, substantially cylindrical stent 40 as shown in FIG. 3 (balloon assembly 30 having been deflated). In another aspect of the invention, the fluid substance is a chosen drug which is delivered only to the portion of the vessel wall isolated by balloon assembly 30 or is incorporated into a stent forming material for release over time from an in situ formed stent.

In general, catheter 28 has a proximal end and a distal end. The distal end makes the initial entry into the vascular system and includes balloon assembly 30. The proximal end is opposite the distal end and may be connected in a conventional manner to an external manifold (as shown in FIG. 20). Conventional manifolds typically include a port (as shown at 110 of FIG. 20) for inserting a guidewire through the catheter, and another port (as shown at 120 of FIG. 20) for injecting fluids into the catheter. A more detailed discussion of a conventional manifold is found in U.S. Pat. No. 4,838,269 to Robinson and the entire disclosure of this patent is incorporated herein by reference.

A guide wire lumen 42 (seen in FIG. 4 and 21) is formed by a substantially cylindrical tube 48 which extends along the length of catheter 28. A second tube 50 encases tube 48 and also extends along the length of catheter 28. Sufficient space is provided between tubes 48 and 50 to create lumen 34 for delivering fluid to balloon assembly 30. As shown in FIG. 20, manifold 100 has at least on fluid injection port 120 in fluid communication with lumen 34 at the proximal end of catheter 28.

As best seen in FIG. 4, balloon assembly 30 is attached at the distal end of the second tube 50 and is thereby placed in fluid communication with lumen 34. Balloon assembly 30 may be secured to second tube 50 by a number of known methods such as brazing, RF welding or by means of an adhesive. The distal end of tube 48 extends completely through balloon assembly 30 thereby providing a pathway through lumen 42 for passing a guidewire 52 through catheter 28.

Balloon assembly 30 includes a single balloon element 56 made of flexible material capable of expanding under pressure. Many materials are known in the art. Balloon element 56 has a particular exterior shape when it is inflated and it is this shape which facilitates the formation of chamber 32 inside vessel 26.

The exterior shape of balloon element 56 has three major components—a proximal ridge seal 58, a distal ridge seal 60 spaced from ridge seal 58, and a stent forming area 62 therebetween. When the balloon element is inflated, the proximal and distal ridge seals 58 and 60 press against the interior wall of the vessel. The stent forming area 62 is depressed inward from ridge seals 58 and 60 and thus, this area 62 does not extend to the vessel wall when the balloon element is inflated. Accordingly, ridge seals 58 and 60 and the depressed area 62 therebetween, along with the interior wall of the vessel, combine to define the chamber 32 when balloon element 56 is inflated.

Area 62 is made from a flexible yet porous material, for example polyethylene, which has a series of openings or perforations 64. These openings 64 allow fluid in the balloon to pass through only after the fluid has reached a predetermined pressure in the balloon. This predetermined pressure is selected such that the balloon is completely inflated before any fluid escapes through the openings. For example, a polyethylene balloon has openings of about 0.003 inches in diameter would operate at about 2 atmospheres. Alternatively the openings could be in the form of microslits which open at pressure and operate as valves. Also, porous materials such as polytetrafluoroethylene which inherently include openings or pores may be used. Also alternatively, the fluid flow through the openings may be controlled by choosing a fluid having sufficient viscosity such that it will only flow through the openings after a predetermined pressure such as 2 ATM has been attained within the balloon. For example, a balloon with 0.003 inches openings including a fluid of about 5 centipoise viscosity would operate at about 2 atmospheres.

The stent forming catheter 28 may be employed alone or in combination with other procedures. For example, catheter 28 may be used to place a stent in a vessel following a PTCA procedure. In one conventional form of a PTCA procedure, for example, a guiding catheter is introduced at an appropriate location in the patient and routed through the vascular system into the aorta and coronary orifice. A relatively flexible guidewire is advanced through the guiding catheter to the artery and then steered into side branches, if necessary, to access a selected lesion. Once the guiding catheter and guidewire have established a path across the lesion, an "over-the-wire" dilatation balloon catheter is passed over the guidewire by inserting the proximal end of the guidewire into the distal end of the balloon catheter and then pushing the balloon catheter over the guidewire until the balloon is adjacent the lesion. The balloon is then inflated by introducing a fluid into the balloon through an inflation lumen in the catheter's shaft. The inflated balloon expands against the blockage to dilate the obstructed blood vessel. The balloon is then deflated and withdrawn over the guidewire. The stent forming catheter 28 may then be advanced over the guide wire for example and positioned in the same region in which the dilation was performed.

The general operation of the catheter 28 is illustrated in FIGS. 1–3. As seen in FIG. 1, the uninflated catheter 28 has been inserted into the body vessel 26 over guide wire 52. Balloon element 56 is then inflated, as shown in FIG. 2, by injecting a fluid (as shown at 150 of FIG. 21) through lumen 34. When the balloon is inflated, the ridge seals 58 and 60 contact the interior vessel wall 26a thereby defining the substantially cylindrical chamber 32. After the pressure in balloon element 56 has reached a predetermined level, the inflation fluid escapes through openings 64 to fill chamber 32. For the disclosed embodiments, the inflation fluid is also the stent forming material which will have a number of desirable properties including the ability to harden when exposed to conditions external to the catheter 28 as already noted. After the fluid in chamber 32 has sufficiently set, the balloon element is deflated by withdrawing fluid from it through lumen 34. Catheter 28 is then removed and a substantially cylindrical stent 40 (shown in FIG. 3) remains in the vessel, having been formed in situ.

Thus, the stent forming catheter 28 of the present invention provides a number of advantages. For example, the in situ formed stent 40 is substantially hollow and thus it does not hinder the flow of blood and other body fluids through vessel 26. Stent 40 may be made from a biodegradable material, such as polylactic acid (PLA) or polymethyl acrylate (PMA) or polyglycolic acid (PGA) or a cyanoacrylate as described hereinabove which will break down and pass through the patient's system over time. The stent material may also be provided with a drug which is time-released into the vessel wall and/or blood stream.

FIGS. 8–11 illustrate another stent forming catheter generally indicated at 28a embodying the present invention. Catheter 28a has many of the same features as catheter 28 shown in FIGS. 1–7 and 21, and these shared features have been assigned the same reference numerals in these later Figures. The following discussion of catheter 28a will focus primarily on the features unique to this embodiment.

Catheter 28a includes a balloon assembly generally indicated at 56a comprising a single inflatable balloon at the distal end of the catheter 28a. When inflated, balloon 56a impinges on the interior vessel wall 26a, as explained in more detail below. Balloon 56a is shown inflated inside vessel 26 in FIGS. 8, 9, 10 and 11.

The in situ stent forming device shown in FIGS. 8–11 has a proximal and a distal end. The proximal end may be connected to a manifold of the type commonly known in the art, such as is shown at FIG. 20. Such a manifold typically has two ports. The first port is a guide wire port in communication with the guide wire lumen 42 and can accommodate the introduction of a guide wire 52. The second port is an inflation/stent port which is in fluid communication with the inflation/stent lumen 34 as will be described in more detail below.

The guide wire lumen runs substantially throughout the length of the in situ stent forming device. This lumen is formed by a substantially cylindrical tube 48, which in an exemplary embodiment may be made of polyethylene. The outside diameter of this tube may be 0.022 inches for example and the inside diameter of the tube may be 0.016 inches for example. The tube may be approximately 135 centimeters in length, which is approximately the length of the device without the guide wire, for example.

Also running from the most proximal portion of the in situ stent forming device to a distal portion of the stent forming device is another piece of tubing 50 which forms the inflation/stent lumen. The tubing 50 also forms the outside skin of the catheter part of the device. This piece of tubing 50, which is also substantially cylindrical, may be made of polyethylene, for example. In an exemplary embodiment, its outside diameter is 0.039 inches and its inside diameter is 0.032 inches, for example. Its length is 0.131 centimeters, for example. At the distal end of the tubing 50 there is attached the balloon 56a. Balloon 56a is attached to the tubing 50 through the use of an adhesive or the like as is known in the art. Balloon 56a is in fluid communication with the inflation/stent lumen 34 and therefore also in fluid communication with the inflation/stent port.

As can be seen when comparing this embodiment with the previously described embodiment, this embodiment is similar except that balloon 56a is different. In this embodiment, balloon 56a has a spiral or helical trough 68 which forms a spiral or helical stent forming region 70. As can be appreciated, this will form a substantially spiral/helical stent. Therefore, this balloon member 56a also comprises two major surface areas. The first area is the balloon contact area, which at each end has ridge seals 58 and 60, but throughout the middle has a spiral shaped vessel contacting region 72. This second major region defines a substantially helical stent forming area 68 for forming a stent. The portion of the balloon within the stent forming area is made of a porous material, for example polyethylene having perforations 64 which only emit fluid when a certain predetermined pressure is obtained within the balloon. Alternately, as in the previous embodiment, the perforations may be always open and the inflation/stent forming fluid may be of a viscosity such that it is only emitted when a high enough pressure is attained within the balloon.

Like the previous embodiment, the device may be inserted into a body lumen such as an artery 26 over a guide wire 52 in an uninflated form (not shown). Then, the device is inflated until the ridge seals 58 and 60 and spiral contacting region 72 come into contact with a vessel wall 26a thereby sealing off a substantially helical area 70 for forming a stent. After the ridge seals and spiral contacting region have come into contact with the vessel wall 26a and the pressure within the balloon is increased, perforations 64 in the stent forming region 70 of the balloon open and release the inflation media, which contains a stent forming material. This stent forming material molds around and into the substantially helical area 68 partitioned off by ridge seals 58, 60 and the spiral contacting region, and then hardens or sets only when outside the balloon. The balloon is then deflated and removed, leaving a substantially helical stent in the artery.

It can be seen by those skilled in the art that the in situ formed stent, which is substantially helical, does not hinder blood flow through the arteries. This stent may be formed of biodegradable materials, such as PLA, which will absorb into the vessel and/or bloodstream over time. This material may also contain a drug for delivery, over time, into the vessel wall and/or bloodstream. This embodiment may be used after a PTCA procedure as described for the previously disclosed embodiment. The procedure, for this embodiment, is substantially the same.

Figure 13:
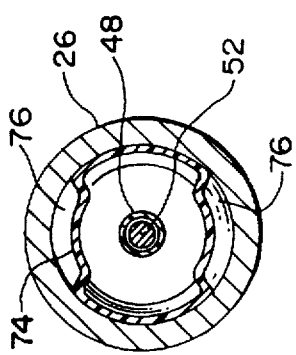
FIG. 13 is a cross sectional view of the catheter shown in FIG. 12, taken along line 13—13.
Figure 14:
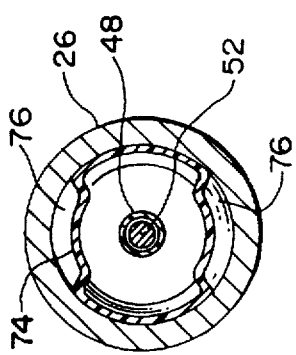
FIG. 14 is a cross sectional view of the catheter shown in FIG. 12, taken along line 14—14.
Figure 15:
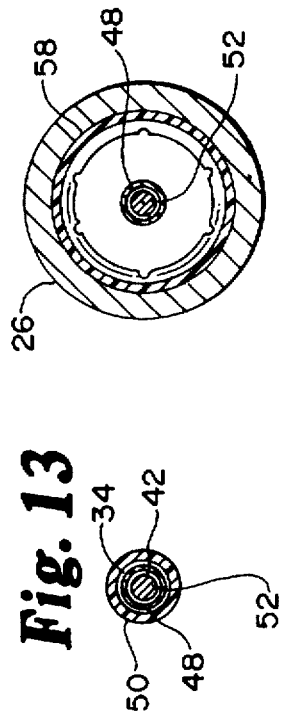
FIG. 15 is a cross sectional view of the catheter shown in FIG. 12, taken along line 15—15.

Referring now to FIGS. 12, 13, 14 and 15, another preferred embodiment of the present invention includes a balloon assembly generally indicated at 56b comprising a single inflatable balloon at the distal end of a catheter generally indicated at 28b. When inflated, balloon 56b impinges on the vessel wall 26a, as explained in more detail below. In FIGS. 12, 13, 14 and 15, the balloon is depicted in an inflated form inside a vessel.

The in situ stent device of this embodiment has a proximal and a distal end. The proximal end may comprise a manifold as known in the art such as is shown at FIG. 20. The manifold typically has two ports; the first port is a guide wire port and is in communication with the guide wire lumen 42 and can accommodate the introduction of a guide wire 52. The second port is an inflation/stent port which is in fluid communication with the inflation/stent lumen 34 which will be described in more detail below.

The guide wire lumen runs substantially throughout the length of the in situ stent forming device. This lumen is formed by a substantially cylindrical tube 48, which in an exemplary embodiment may be made of polyethylene. The outside diameter of this tube may be 0.022 inches and the inside diameter of the tube may be 0.016 inches for example. The tube is approximately 135 centimeters in length, which is approximately the length of the device without the guide wire, for example.

Also running from the most proximal portion of the in situ stent forming device to a distal portion of the stent forming device is another piece of tubing 50 which forms the inflation/stent lumen. The tubing 50 also forms the outside skin of the catheter part of the device. This piece of tubing 50 which is also substantially cylindrical, may be made of polyethylene, for example. In an exemplary embodiment, its outside diameter is 0.039 inches and its inside diameter is 0.032 inches. Its length is 0.131 centimeters, for example. At the distal end of the tubing 50 there is attached the balloon 56b. Balloon 56b is attached to tubing 50 through the use of an adhesive or the like as is known in the art. Balloon 56b is in fluid communication with the inflation/stent lumen 34 and therefore also in fluid communication with the inflation/stent port.

As can be seen when comparing this embodiment with the previously described embodiments, this embodiment is similar except that the balloon 56b is different. In this embodiment, the balloon member has two crossed spiral or helical troughs 74 which forms a crossed double helical stent forming region 76. As can be appreciated, this will form a substantially crossed double helical stent. Therefore, this balloon member 56b also comprises two major areas. The first area is the balloon contact area, which at each end has ridge seals 58 and 60, but throughout the middle has diamond shaped vessel contacting regions 78. The second major region is the stent forming region 74 which defines a substantially crossed double helical stent forming trough area for forming a stent. The portion of the balloon within the stent forming area is made of a porous material, for example polyethylene which has perforations 64 which only emit fluid when a certain predetermined pressure is obtained within the balloon. Alternately, as in the previous embodiment, the perforations may be always open and the inflation/stent forming fluid may be of a viscosity such that it is only emitted when a high enough pressure is attained within the balloon.

Like the previous embodiments, the device may be inserted into a body lumen, such as an artery 26, over a guide wire 52 in an uninflated form (not shown). The device is then inflated until the ridge seals 58 and 60 and diamond-shaped contact regions 78 come into contact with the vessel wall 26a thereby sealing off a substantially crossed double helical area 74 for forming a stent. After the ridge seals and diamond-shaped contact regions have come into contact with the vessel wall 26a and the pressure within the balloon is increased, the perforations 64 in the stent forming regions 74 of the balloon open and release the inflation media, which contains a stent forming material. This material cures or hardens only outside the balloon as already noted. This stent forming material molds around and into the substantially crossed double helical area 74 partitioned off by the ridge seals 58, 60 and the diamond shaped vessel contacting regions, and then hardens. The balloon is then deflated and removed, leaving a substantially crossed double helical stent in the artery.

It can be seen by those skilled in the art that the in situ formed stent, which is substantially crossed double helical, does not hinder blood flow through the arteries. This stent may be formed of biodegradable materials, such as PMA which will absorb into the vessel and/or bloodstream over time. These materials may also contain a drug for delivery, over time, into the vessel wall and/or bloodstream. This embodiment may be used after a PTCA procedure as described for the previously disclosed embodiment. The procedure, for this embodiment, is substantially the same.

Referring now to FIGS. 16, 17, 18 and 19, another preferred embodiment of the present invention includes a balloon assembly 56c comprising a single inflatable balloon at the distal end of the catheter 28c. When inflated, balloon 56c impinges on the vessel wall 26a, as explained in more detail below. In FIGS. 16, 17, 18 and 19 the balloon is depicted in an inflated form inside a vessel.

The in situ stent device of this embodiment has a proximal and a distal end. The proximal end may comprise a manifold as known in the art such as is shown at FIG. 20. The manifold typically has two ports; the first port is a guide wire port and is in communication with the guide wire lumen 42 and can accommodate the introduction of a guide wire 52. The second port is an inflation/stent port which is in fluid communication with the inflation/stent lumen 34 which will be described in more detail below.

The guide wire lumen runs substantially throughout the length of the in situ stent forming device. This lumen is formed by a substantially cylindrical tube 48, which in an exemplary embodiment may be made by polyethylene. The outside diameter of this tube may be 0.022 inches and the inside diameter of the tube may be 0.016 inches, for example. The tube is approximately 135 centimeters in length, which is approximately the length of the device without the guide wire, for example.

Also running from the most proximal portion of the in situ stent forming device to a distal portion of the stent forming device is another piece of tubing 50 which forms the inflation/stent lumen. The tubing 50 also forms the outside skin of the catheter part of the device. This piece of tubing 50 which is also substantially cylindrical, may be made of polyethylene, for example. In an exemplary embodiment, its outside diameter is 0.039 inches and its inside diameter is 0.032 inches. Its length is 131 centimeters, for example. At the distal end of the tubing 50 there is attached the balloon 56c. Balloon 56c is attached to the tubing 50 through the use of adhesives or the like as is known in the art. Balloon 56c is in fluid communication with the inflation/stent lumen 42 and therefore also in fluid communication with the inflation/stent port.

As can be seen when comparing this embodiment with the previously described embodiments, this embodiment is similar except that the balloon 56c is different. In this embodiment, the balloon has a substantially cylindrical stent forming region 80 with "bumps" 82 which form a substantially cylindrical stent forming region 84. As can be appreciated, the bumps 82 will form a substantially cylindrical stent with perforations. Therefore, this balloon member 56c also comprises two major areas. The first area is the balloon contact area, which at each end has ridge seals 58 and 60, but throughout the middle has bumps 82 which contact the vessel wall 26a. This second major region is the stent forming region 84 which defines a substantially cylindrical stent forming area with bumps 82 for forming a perforated stent. The portion of the balloon within the stent forming area is made of a porous material, for example polyethylene with perforations 64 which only emit fluid when a certain pressure is obtained within the balloon. Alternately, as in the previous embodiment, the perforations may be always open and the inflation/stent forming fluid may be of a viscosity such that it is only emitted when a high enough pressure is attained within the balloon.

Like the previous embodiment, the device may be inserted into a body lumen such as an artery 26 over a guide wire 52 in an uninflated form (not shown). Then, the device is inflated until the ridge seals and bumps come into contact with a vessel wall 26a thereby sealing off a substantially cylindrical area with perforations 64 for forming a stent. After the ridge seals and bumps have come into contact with the vessel wall 26a and the pressure within the balloon is increased, the perforations 64 in the stent forming region 84 of the balloon open and release the inflation media, which contains a stent forming material. This stent forming material molds around and into the substantially cylindrical area with perforations 64 partitioned off by the ridge seals 58, 60 and the bumps, and then hardens or sets. The balloon is then deflated and removed, leaving a substantially cylindrical stent with perforation in the artery.

It can be seen by those skilled in the art that the in situ formed stent, which is substantially cylindrical with perforations, does not hinder blood flow through the arteries. This stent may be formed of biodegradable materials, such as PLA, which will absorb into the vessel and/or bloodstream over time. These materials may also contain a drug for delivery, over time, into the vessel wall and/or bloodstream. This embodiment may be used after a PTCA procedure as described for the previously disclosed embodiment. The procedure, for this embodiment, is substantially the same.

The presently disclosed embodiments of the invention are beneficial over the prior art. These devices are capable of an extremely low profile, because of their single balloon construction. Therefore, when deflated, the balloon has an extremely low profile and is able to travel through very narrow regions of a patient's vascular system. This is also extremely useful when, due to vasoconstriction or other types of collapse of the vessel wall after PTCA, or before PTCA, the portion of the artery to which the stent must be delivered is extremely narrowed. Additionally, this device may be used to deliver stent materials now known, or developed in the future, which are capable of delivering a drug to the vessel wall. The stent that is delivered has many advantages over the prior art. Because the stent may be biodegradable, and/or biocompatible, no strict drug regime will be necessary after implantation, as is commonly required with other prior art stents, especially metal stents. As described above, although PTCA has been highly successful and a great advance in the fight against obstructive coronary artery disease, patients may, in some cases, have some problems. These problems, such as the forming of flaps after the PTCA, or vasoconstriction or long term restenosis, can be cured using the present invention. The stent delivered may be used to temporarily hold up flaps until they can heal against the vessel wall. This device may also be used to deliver a drug over a long period of time and prevent restenosis. After all of the adverse symptoms sometimes encountered following a PTCA procedure have been cured, the stent in biodegradable form slowly dissolves into the patient's body.

It is also contemplated that the device can deliver a permanent stent that is located within the patient's body and is biocompatible. This would also reduce the need for long term drug regime.

Further, the stent form may be extremely flexible. This would prevent certain problems with prior art stents, such as dissections of artery. In and around the coronary arteries there is much movement due to the beating of the heart. Therefore, it is highly desirable to have a flexible, non-rigid stent. The formed stents contemplated by the present invention, may be highly flexible due to the disclosed shapes and/or materials and therefore well suited to be placed in coronary arteries unlike prior art rigid stents. Although the above embodiments have been described in connection with an "over-the-wire" type design, it is also contemplated that the guide wire lumen may be eliminated and a guide wire tip, as is known in the art, may be secured to the end of the balloon. Eliminating the guide wire lumen reduces the profile of the uninflated balloon, thereby allowing it to be maneuvered through even smaller portions of a patient's vascular.

The foregoing description of the exemplary and preferred embodiments of the present invention has been presented for purposes of illustration and description. They are not intended to be exhaustive or to limit the invention to the precise forms disclosed, and obviously many modifications and variations are possible in light of the above teachings. The embodiments were chosen and described in order to best explain the principal of the invention and its practical applications and to thereby enable others skilled in the art to best utilize the invention in various embodiments and with various modifications as are suited to the particular use contemplated.

It is intended that the scope of the invention be defined by the following claims, including all equivalents.

I claim:

1. A device consisting of:
 a. an elongated tubular member having a proximal end and a distal end;
 b. a guide wire lumen disposed within the tubular member;
 c. an inflatable balloon member located at the distal end of the tubular member and extending distally therefrom, said balloon member having a proximal end and a distal end, said balloon member being made of a flexible material and further comprising:
   i. at least two spaced ridge seals formed upon at least partial inflation of said balloon member, said ridge seals in combination with a portion of the balloon member therebetween defining an isolation zone therebetween and exterior of the balloon member, said ridge seals for being positioned in use against a vessel wall such that in situ said isolation zone further defines a stent forming chamber; and
   ii. infusion ports in fluid communication with the tubular member, said infusion ports being located at the portion of the balloon member between the two ridge seals, the guide wire lumen further extending through said balloon member, said guide wire lumen in combination with the distal end of the balloon member defining a distal balloon seal; and
 d. a fluid injection port in combination with curable, fluid stent forming material, said fluid injection port being in fluid communication with the tubular member at the proximal end of the tubular member for delivery of the stent forming material, said infusion ports being small enough to allow the balloon member to inflate yet large enough at increased inflation pressure to allow the stent forming material to exit the balloon member through the infusion ports directly into the isolation zone, whereby the stent forming material is delivered through the fluid injection port, the tubular member and the infusion ports directly into the isolation zone to form a stent in situ in the stent forming chamber.

2. The device of claim 1 wherein the stent forming material comprises a cyanoacrylate.

3. The device of claim 2 wherein the formed stent further includes at least one drug.

4. The device of claim 1 wherein the stent forming material further includes at least one drug.

5. The device of claim 4 or 3 wherein the drug is released over time in an area to be treated.

6. The device of claim 1 further comprising a guide wire tip located at and extending distally from the distal end of the tubular member.

7. The device of claim 1 wherein the guide wire lumen is disposed substantially coaxially within the tubular member.

8. The device of claim 6, 7 or 1 wherein the isolation zone is substantially cylindrical.

9. The device of claim 1 wherein the formed stent is temporary.

10. The device of claim 1 wherein the formed stent is permanent.

11. The device of claim 1 wherein the formed stent is biodegradable.

12. The device of claim 1 wherein the infusion ports remain closed until the balloon is inflated to at least a predetermined pressure.

13. The device of claim 1 wherein the viscosity of the stent forming material, is such that it only travels through the infusion ports when the balloon is inflated to at least a predetermined pressure.

14. An in situ stent forming system comprising:
 a. a device consisting of:
   i. an elongated tubular member having a proximal end and a distal end;
   ii. a guide wire lumen disposed within the tubular member;
   iii. an inflatable balloon member located at the distal end of the tubular member and extending distally therefrom, said balloon member having proximal and distal ends, being made of a flexible material and further comprising:

a) at least two spaced ridge seals formed upon at least partial inflation of said balloon member, said ridge seals defining an isolation zone therebetween exterior of the balloon member, said ridge seals being positioned in use against a vessel wall such that in situ said isolation zone further defines a stent forming chamber; and b) infusion ports in fluid communication with the tubular member, said infusion ports being located at an area of the balloon member between the two ridge seals, the guide wire lumen of the tubular member further extending through said balloon member, said guide wire lumen in combination with the distal end of the balloon member defining a distal balloon seal; and iv. a fluid injection port in fluid communication with the tubular member at the proximal end of the tubular member; and b. a source of curable fluid stent forming material connected to the fluid injection port, said infusion ports being small enough to allow the balloon member to inflate yet large enough at increased inflation pressure to allow the stent forming material to exit the balloon member directly into the isolation zone, whereby a curable fluid stent forming material is delivered through the fluid injection port, the tubular member and the infusion ports directly into the isolation zone to form a stent in situ in the stent forming chamber.

15. The device of claim 14 further comprising a guide wire tip located at and extending distally from the distal end of the tubular member.

16. The device of claim 14 wherein the guide wire lumen is disposed substantially coaxially within the tubular member.

17. The device of claim 14, 15 or 16 wherein the isolation zone is substantially cylindrical.

* * * * *